(12) United States Patent
Schoene et al.

(10) Patent No.: US 7,967,642 B2
(45) Date of Patent: Jun. 28, 2011

(54) CONNECTOR IN THE FIELD OF TELECOMMUNICATIONS

(75) Inventors: Stefan Schoene, Bochum (DE);
Gerardus A. C. A. Nuiten, Neuss (DE);
Christian Weinmann, Alsdorf (DE);
Hermanus Franciscus Maria Van Meijl, Someren-Eind (NL); Mathieu Nesme, Sallanches (FR); Guy Metral, Cluses (FR)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/680,948

(22) PCT Filed: Sep. 30, 2008

(86) PCT No.: PCT/US2008/078258
§ 371 (c)(1),
(2), (4) Date: Mar. 31, 2010

(87) PCT Pub. No.: WO2009/046000
PCT Pub. Date: Apr. 9, 2009

(65) Prior Publication Data
US 2010/0273357 A1  Oct. 28, 2010

(30) Foreign Application Priority Data
Oct. 4, 2007 (EP) .................................. 07019489

(51) Int. Cl.
*H01R 33/00* (2006.01)
(52) U.S. Cl. ....................................... 439/660

(58) Field of Classification Search .................. 439/686, 439/660, 676, 695
See application file for complete search history.

(56) References Cited

U.S. PATENT DOCUMENTS

| | | | | |
|---|---|---|---|---|
| 4,236,779 A * | 12/1980 | Tang | ...................... | 439/607.48 |
| 5,192,226 A * | 3/1993 | Wang | .......................... | 439/502 |
| 5,199,904 A * | 4/1993 | Wharton | ...................... | 439/668 |
| 5,478,250 A * | 12/1995 | Hoffman | ...................... | 439/142 |
| 5,957,720 A | 9/1999 | Boudin | | |
| 6,160,485 A * | 12/2000 | Krakovich | .................... | 340/635 |
| 6,267,617 B1 | 7/2001 | Nozick | | |
| 6,348,035 B1 * | 2/2002 | Takami | ...................... | 600/132 |
| 6,793,515 B1 | 9/2004 | Gwiazdowski et al. | | |
| 6,799,981 B1 * | 10/2004 | Yu | .............................. | 439/133 |
| 7,035,112 B2 * | 4/2006 | Chen | ............................ | 361/752 |
| 7,112,086 B1 | 9/2006 | Wu | | |
| 7,413,464 B1 * | 8/2008 | Chen | ............................ | 439/404 |
| 7,572,133 B2 * | 8/2009 | Hughes et al. | ................ | 439/181 |
| 7,637,780 B2 | 12/2009 | Schoene et al. | | |
| 7,641,610 B2 * | 1/2010 | Nakamura et al. | ............ | 600/132 |
| 2004/0229517 A1 | 11/2004 | Bush et al. | | |
| 2006/0094281 A1 | 5/2006 | Dang | | |

(Continued)

FOREIGN PATENT DOCUMENTS

DE 100 57 869 C1 8/2002
(Continued)

*Primary Examiner* — Jean F Duverne
(74) *Attorney, Agent, or Firm* — Janet A. Kling

(57) ABSTRACT

A connector (10) in the field of telecommunications has contacts (12) with which wires are connectable inside the connector (10), and at least three wire openings (16, 116), each opening (16, 116) being adapted to accommodate at least two wires and exposed on an outside of the connector (10) distal from the contacts, the wire openings (16, 116) being exposed in at least three different directions.

10 Claims, 2 Drawing Sheets

U.S. PATENT DOCUMENTS

| | | | |
|---|---|---|---|
| 2006/0110983 A1* | 5/2006 | Muench et al. | 439/660 |
| 2008/0176453 A1* | 7/2008 | Minich et al. | 439/660 |
| 2008/0293305 A1* | 11/2008 | Quenneville et al. | 439/660 |
| 2010/0015844 A1* | 1/2010 | De Dios Martin et al. | 439/395 |
| 2010/0087100 A1* | 4/2010 | De Blieck et al. | 439/680 |

FOREIGN PATENT DOCUMENTS

| | | |
|---|---|---|
| EP | 0 233 397 A1 | 8/1987 |
| EP | 0 935 314 A2 | 8/1999 |
| EP | 1 311 022 A1 | 5/2003 |
| EP | 0 921 603 B1 | 2/2007 |

* cited by examiner

CONNECTOR IN THE FIELD OF TELECOMMUNICATIONS

CROSS REFERENCE TO RELATED APPLICATIONS

This application is a national stage filing under 35 U.S.C. 371 of PCT/US2008/078258, filed Sep. 30, 2008, which claims priority to European Application No. 07019489.9, filed Oct. 4, 2007, the disclosure of which is incorporated by reference in its/their entirety herein.

TECHNICAL FIELD

The invention relates to a connector in the field of telecommunications providing an increased versatility regarding the connection of wires.

BACKGROUND

In the field of telecommunications, and in the field of data transmission and processing, numerous connections are established by telecommunications and/or data lines. These connections can be made by wires, for example copper wires.

Plural wires can be integrated with a cable and can be put together at a connector, such as a plug or a socket. By connecting two connectors of this type with each other, plural connections between the wires, which are connected with each of the connectors, are established. Such a type of connection can also be used in networks, such as local area networks, for any connections between devices being part of the network. Such a network may have an outlet in a work area and a patch panel in a data room. Connectors may be mounted in the outlets and/or the patch panels. Typical connectors are described in ICE 60603-7.

In the field of telecommunications and data transmission recent advances in ADSL-technology allow transmission of at least two different signals on a single telecommunications line. This is achieved by transmitting the different signals at different frequencies along the same line. In particular, on the subscriber side, separate voice and data signals are combined and sent to the central office via the same transmission line where it may be split. The voice signal is then directed to the other subscriber(s) on the telephone call, and the data signal is directed to the other subscriber(s) participating in the data exchange. For the transmission of voice and data signals to the subscriber, separate voice and data signals are combined at the central office, sent to the subscriber and split at the subscriber side.

Particularly in connection with ADSL technology, the rates at which telecommunications and data signals are transmitted by telecommunications modules have increased remarkably resulting in increased cross-talk effects. The term "cross-talk" describes an effect in which the contacts of a telecommunications module act as small antennae, which transmit an interfering signal to adjacent contacts. Generally, the interfering signals are transmitted by a pair of wires and, therefore, by a pair of adjacent contacts. Thus, cross-talk between the contacts of a single pair is not an issue. However, cross-talk between the contacts of adjacent pairs should be reduced as far as possible.

The contacts in conventional jack connectors may be in close proximity to one another. If these jack connectors are used in high performance communication systems, cross cross-talk between adjacent conductor pairs may occur. As regards cross-talk between pairs of wires, such cross-talk is reduced by twisting the pairs. Moreover, plural twisted pairs, which may be integrated in a cable, may be shielded from each other and/or twisted themselves. The shielding of an individual wire pair may be formed by a foil shielding, in other words, a metal foil or metalized foil formed around a twisted pair. As an alternative, individual pairs may be shielded by a braid. Finally, cross-talk between adjacent cables may be reduced by shielding the cables. In this context, the shielding of individual wire pairs may be formed as a foil shielding, and the shielding of the cable may be formed by a braid. Moreover, the cable may additionally have a drain wire.

U.S. Pat. No. 6,267,617 B1 describes a low current outlet having contact pins and an organizer cap, which, on being fixed to a base, establishes electrical contact between wires and the contact pins. The cap is provided with wire guides extending parallel to each other.

US 2004/0229517 A1 is related to a jack having a terminal housing with a base through which one or more wire management tunnels extend. The tunnels may have openings facing opposite directions.

U.S. Pat. No. 5,957,720 A describes a socket having a connecting pusher which may be pushed by jaws fixed on the socket so as to engage wires arranged in the connecting pusher with insulation displacement contacts.

U.S. Pat. No. 6,793,515 B1 is related to a connecting cable having a cable manager with guides adapted to accommodate individual wires.

SUMMARY OF THE INVENTION

The invention provides a connector in the field of telecommunications which has an improved versatility regarding the connection of wires.

BRIEF DESCRIPTION OF THE DRAWINGS

The invention will be described hereinafter in part by non-limiting examples thereof and with reference to the drawings, in which.

DETAILED DESCRIPTION OF THE PREFERRED EMBODIMENTS

Figure 1:
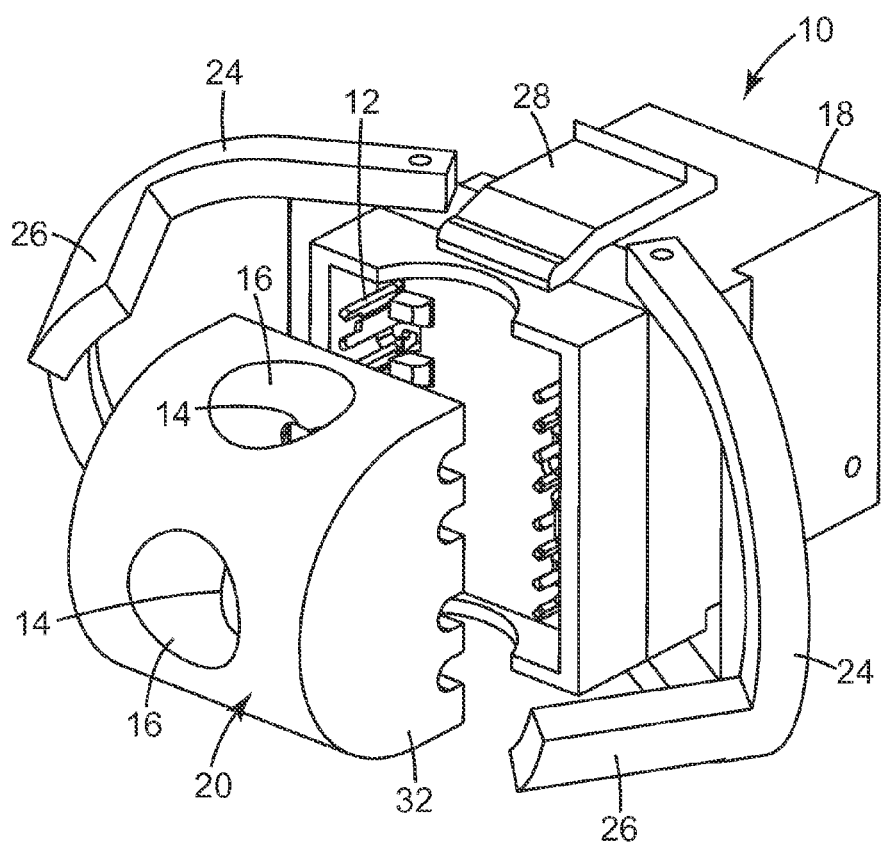
FIG. 1 shows a perspective rear view of a connector according to the invention, partly dissembled.

The connectors described herein have contacts with which wires are connectable. The wires may be connectable with the contacts "inside" the connector, i.e. the interfaces between the wires and the connectors may, during use of the connector, be fully "hidden" and/or fully surrounded by parts of the connector's housing. Those portions of the contacts, where wires are connectable, may, for example, be formed as insulation displacement contacts, as wire wrap contacts or in any other suitable manner. The contacts may have portions exposed outside the connector, so that a complementary connector also having contacts is connectable with the connector such that the contacts of the connectors are in electrical contact. By way of example, the connector described herein may be a RJ45 type connector or a connector in line with ICE 60603-7.

The wires, which are connectable with the contacts of the connector, may be integrated with a cable and the connector described herein may have at least three wire openings for inserting at least two wires through each opening. The wire openings may, for example, be adapted to accommodate two wires, i.e. a pair of wires, which may be twisted, four wires, i.e. the two pairs, or more wires. Moreover, at least one wire opening may be adapted to accommodate a cable, with which the wires are integrated. A cable may, for example, have four twisted wire pairs integrated therewith. The wire pairs may be shielded from each other, and a shielding as well as an electrical insulation may be provided around the wire pairs. The connectors described herein may be advantageous in that the "complete" cable may be inserted through a wire opening and guided in a suitable cable guide. A "complete" cable may have plural twisted wire pairs, for example, four wire pairs, shielding for the individual pairs and/or the cable shielding around all pairs, possibly a drain wire and, for example, as the outermost layer, an insulation. When a wire opening is adapted to accommodate a "complete" cable, it can substantially be ruled out that the shielding and electrical insulation needs to be removed from the cable until the location, where the wires are separated from each other to individually connect them with contacts. In this context, it is noted that cables, as described above, may be formed "substantially balanced" by providing twisted wire pairs, twisting the twisted pairs themselves and providing appropriate shielding. This substantially balanced state is disturbed when the individual pairs, or even wires, are separated from each other. In other words, the desired, substantially balanced state may substantially be maintained if the wire openings are adapted to accommodate a "complete" cable. These effects may be supported by an appropriate arrangement of the contacts of the connector, which allow guiding the wires to the individual contacts with as few crossings of twisted wire pairs as possible.

One or more wire openings may be adapted to allow the insertion of fewer wires then wires integrated with a cable. The wire openings, which may, for example, be smaller in cross-section than the cable, may then allow to remove the insulation and shielding of cable and the separation of wires or wire pairs from each other at a defined location. In certain applications it has been found that it would have drawbacks to insert the cable including insulation and shielding too far into the connector and towards the contacts. There is, for example, a certain risk of a short-circuit when a cable shielding gets into electrical contact with the contacts of the connector. Thus, in these cases, insulation and shielding of a cable may be removed at the end of the cable for a certain distance, and the wires or wire pairs may be separated from each other and inserted into the connector, through the one or more wire openings, individually. In this situation, a wire pair, possibly together with its individual shielding, such as a foil shielding may be inserted into the connector through the one or more openings. This may be advantageous as the twisted wire pair may maintain the twisted state and may also be guided in this state, which may be beneficial from the viewpoint of shielding.

The wire openings may be exposed on an outside of the connector distal from the contacts. The wire openings can also be said to be exposed to a side where an incoming cable is to be connected with the connector. This side may be described to be generally opposite a side where a complementary connector is to be inserted. Thus, the wire openings exposed on the outside of the connector may be described to be remote or distal from the contacts. As mentioned, any connections between individual wires and the contacts may be formed within the connector.

The wire openings may be formed by a relatively simple opening, through hole or bore that serves to allow the insertion of wires or the cable in a certain direction at that point, where the opening, through hole or bore is formed.

The advantageous effect of increased versatility is supported by the aspect that the wire openings are orientated in at least three different directions. Firstly, the wire openings are exposed on the outside of the connector. Thus, a cable or wire may be inserted into an appropriate opening from outside the connector. In this context, it may be advantageous to provide openings being orientated in at least three directions to allow cables coming from at least three different directions, to be safely and reliably connected with the connector. Due to the orientation of the at least three openings, the appropriate one, i.e. the one being orientated with the most "coincidence" with the direction of the wire or cable, may be chosen to insert the wire or cable. In particular, cables arriving from underneath the floor, under a ceiling, in ducts or from behind panels, may advantageously be inserted into the connector with their orientation being substantially maintained up to a position inside the connector. This may minimize the occurrence of undesired bendings of the cable, which is particularly advantageous when insulation and/or shielding have been removed from the cable. This is because in this state, i.e. with insulation and/or shielding removed, the desired arrangement of the wires may be difficult to maintain.

The at least three openings may, for example, be exposed in different radial directions from a center region of the connector or a location where it is intended to disintegrate the wires of the cable and separate individual wires from each other.

Thus, disadvantageous curvatures at the location of entry into the connector may substantially be avoided. Moreover, the wires or the complete cable may be guided particularly close to the contacts, the wires may be separated from each other there and the connections with the contacts may be made relatively close to this location. In particular, any unavoidable bending, to bring the wires into a proper orientation relative to the contacts, may be done in a controlled manner, such as within the connector and by providing a defined orientation of recesses guiding the individual wires (described in more detail below) and other guides. In particular, the complete cable may not have to be bent at all. Rather, the necessary bending of the wires may be done at that point, where the wires are separated from each other. For example, the unavoidable bendings of the wires may be as close as possible to the contacts of the connector.

Thus, reliable connections can be made between the contacts and the wires, the twisting of the wire pairs and the separation between wire pairs can be maintained up to a location very close to the contacts, and the shielding of the cable may be kept up to this point. Thus, the occurrence of cross-talk may be minimized. Moreover, the well defined positioning of the individual wires and the substantial minimization of disarrangements and misalignments of wires secures the transmission performance of the wires.

The connector described herein may be mounted on printed circuit boards. Also in such a case, a cable may be connected with the connector as described above. As an alternative, or in addition to such a cable, a cable could be connected with conductors printed on the printed circuit board and connected with contacts of the connector. The printed circuit boards may be provided in active network equipment such as routers. Moreover, the connectors may be mounted on patch panels and outlets that may be provided in walls or cable ducts.

The wire openings may be arranged in pairs or groups of four, the openings of one pair or group being exposed in the same direction. The group of openings may be adapted to allow the insertion of all wires of a cable through the openings of a single group. Thus, substantially all wires of a cable, arriving at the connector with a particular orientation, may substantially keep this orientation through the openings and up to a location inside the connector. This also applies when one or more openings are adapted to accommodate a "complete" cable. Also in this case, the cable may arrive from any one of at least three different directions and may advantageously not have to be bent at the point of entry into the connector. Moreover, when the openings are arranged in pairs or groups of four, each opening may, for example, be adapted to accommodate half or a quarter of the number of wires which are present in a cable. For example, in a cable having eight wires, i.e. four pairs, four wires, i.e. two pairs can be inserted into each opening of a pair of openings. When a group of four openings is present, two wires, i.e. one pair, may be inserted into each opening of a group of four openings. With such a structure, the wires may advantageously be kept spaced from each other already at their point of entry into the connector. In this manner, cross-talk may be minimized.

A guide may be formed adjacent at least one wire opening and may have a certain extension in the direction of the wire or cable to be guided, to define the direction and shape of the wire or cable substantially throughout the extension of the guide. Thus, the guide may extend substantially straight, curved or angled. Wherever curves and/or angles are present, when the guide is adapted to guide the complete cable, the cable is advantageously bent as a complete cable, so that misalignments of the individual wires are unlikely, so that deterioration of the transmission performance and of the cross-talk properties may be minimized. The wire or cable guide may be formed by structures, such as partitions, webs and/or lugs adapted to keep individual wires or groups of wires apart from each other. Moreover, channels, which may have a closed cross-section, may be formed in the connector to guide individual wires or groups of wires to those contacts with which they are to be connected. In addition to wire or cable guides, or alternatively, the connector may have a colour coding to assist the person connecting wires with the connector in making the correct connections.

At least one guide may be adapted to accommodate a cable with which all wires connectable with the contacts of the connector are integrated. Thus, a "complete" cable may be guided by the guide and the possibility of misarranging individual wires is particularly low. However, as indicated above, it may also be advantageous to adapt at least one guide to accommodate fewer wires, such as a single wire pair.

It may be advantageous to provide the connector with a housing and at least one guide piece. At least one wire opening may be formed in the guide piece. With these separated components, both the housing and the guide piece may be designed with a specific focus on the functionality of the component. For example, the housing may be designed to accommodate the contacts, the guide piece and, for example, any structures, such as latch hooks, screw openings or similar structures which allow the connector to be mounted to a patch panel, an outlet or similar surrounding as described above. Moreover, the guide piece may have wire or cable guides as mentioned above with any suitable structure, including those exemplary structures mentioned above.

The guide piece may be adapted to be moved towards the contacts to connect the wires with the contacts. This movement and the resulting connection of wires may be effected manually so that there may be no need to provide and use specific tools.

The guide piece may not only have openings and adjacent guides but also at least one recess for accommodating at least one individual wire. The recess may be facing the contacts so that an individual wire may be accommodated in a manner to support its connection with a contact. The recesses that are adapted to guide individual wires may be formed of any other suitable structures for guiding individual wires, such as ribs or channels.

The contacts may be formed as insulation displacement contacts having a contact slit, into which the wire is pushed to cut the insulation of the wire and allow the legs defining the contact slit to contact the metal part of the wire. When the wires are accommodated in recesses, as described above, it has been found advantageous to push the wires into the contact slits in this accommodated position. In this connection, it may be advantageous to provide at least one slot for accommodating at least one contact in the guide piece. Moreover, the one or more slots may be used, together with the contacts accommodated therein, to guide the guide piece when it is moved towards the contacts. However, alternatively or in addition, further guiding elements may be provided on the connector to guide the movement of the guide piece.

Moreover, the above-described step of pushing the wire into the contact slit while accommodated in the recess, may be performed readily when at least one slot and at least one recess intersect each other.

As indicated above, the guide piece may be adapted to be moved towards the contact to push the wires into the contacts. Thus, it may be advantageous to provide the housing with at least one drive piece adapted to drive the guide piece to the contacts. Such a drive piece may assist the operator connecting the wires with the contacts in establishing the connections.

It may be particularly advantageous to form at least one drive piece as a pivotable flap having at least one projection adapted to drive the guide piece when the flap is pivoted. This allows an especially easy actuation of the drive piece to move the guide piece towards the contact. Moreover, through the action of the projection, a lever effect may be used.

It has been found in tests with the connector described herein that the guide piece can be moved towards the contacts relatively easily, when two projections are provided. Two projections may, moreover, be provided in a manner to locate at least one wire opening between two projections. Thus, an easy actuation of the guide piece may be combined with a ready access to the wire openings.

Whereas the connectors described herein may be provided as plugs or male connectors, preferred embodiments of connectors may be formed as jacks or sockets, i.e. female connectors.

Turning now to FIG. 1, which is a perspective rear view (i.e. from the side where the cable enters the connector) of the connector 10, partly disassembled. The side, where a cable (not shown) is inserted into the connector 10, for example through an opening 16, is facing the viewer of FIG. 1. Therefore, the generally opposite side, where a complementary connector may be inserted, is not visible in FIG. 1. However, as will be readily apparent to those skilled in the art, a housing 18 of the connector 10 may define a generally rectangular opening, within which contacts are exposed to allow the contacts of a complementary connector (not shown) to be electrically contacted. The housing may be provided with latch hooks 28 or similar structures to allow mounting the connector 10 to an appropriate surrounding. This may, for example, be performed by attaching the connector 10 to a panel from the rear side, so that the latch hook visible in FIG. 1 will protrude to the front side. When the panel has two substantially parallel walls, the latch hook protruding through the rear wall may be hidden behind a front wall.

Inside the connector 10, those portions of the contacts 12, where wires (not shown) are connectable, are shown. These portions may be formed as insulation displacement contacts. A guide piece 20 having, in the embodiment shown, three openings 16 with adjacent guides 14 (one of them being formed on the underside and not visible in FIG. 1) may be moveable towards the contacts 12. As described in more detail below with reference to FIG. 2, a cable having a plurality of wires, with shielding and insulation around all the wires, may be inserted into either one of the cable guides 14 through the respective opening 16 visible in the figure. In the embodiment shown, the guide piece 20 is formed as a type of semi-cylinder with recesses 22 (see FIG. 2) adapted to accommodate individual wires being formed on the flat face and wire openings 16 being formed at three different positions along the curved face.

The connector shown in FIG. 1 has two drive pieces in the form of pivotable flaps 24, each having a projection 26. When a cable has been inserted through cable guide 14, and the individual wires have been accommodated in the recesses 22 (see FIG. 2), the guide piece 20 may be placed in close proximity to the contacts 12, the pivotable flaps may be pivoted towards the guide piece 20, and the projections 26 may be engaged the guide piece 20 to push it towards the contacts 12 when the pivotable flaps 24 are approaching their final position shown in FIG. 3. Generally, the pivotable flaps 24 may be pivotable about an axis perpendicular to the direction in which the guide piece 20 is to be moved.

Figure 2:
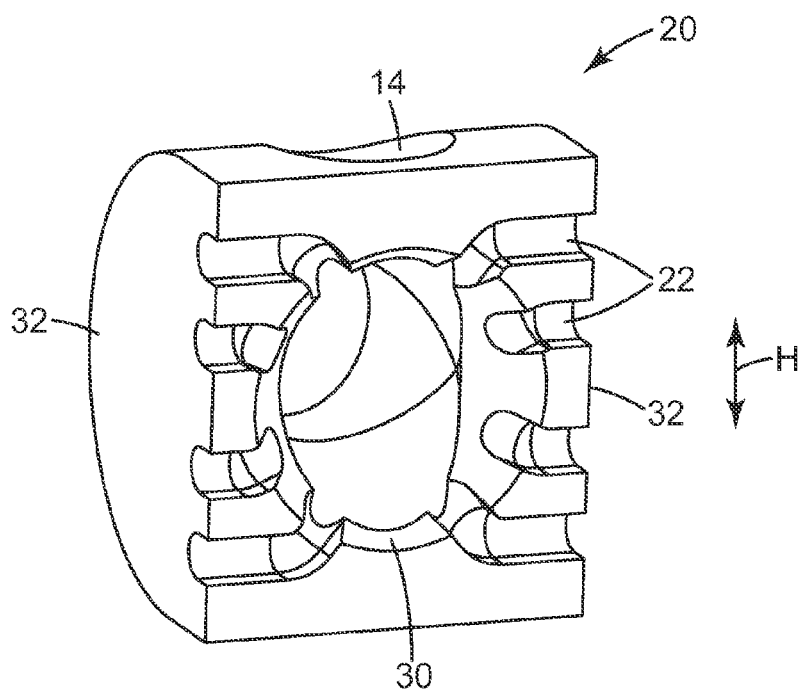
FIG. 2 shows a perspective view of a guide piece of the connector of FIG. 1.

As can be seen in FIG. 1, the cable guides 14 may have a certain extension from the semi-cylindrical surface visible in FIG. 1 towards the inside of the guide piece 20 visible in FIG. 2. In other words, the guides 14 may have a substantially cylindrical inner wall, by which the cable may be guided. Moreover, the guide piece 20 shown in FIG. 1 may additionally have openings formed at one or both (semi-circular) side faces, i.e. those faces directed to the pivotable flaps 24. Moreover, one or both pivotable flaps 24 may be formed with suitable openings to allow access to the above-described laterally open wire openings, which are not shown in FIG. 1. With this modification, the cable to be connected with the connector 10 may not only arrive at the connector 10 from the rear side, the top and the bottom, as seen in FIG. 1, but also from one or both of the lateral sides.

FIG. 2 shows the guide piece 20 of FIG. 1 from the side facing the contacts 12 (see FIG. 1). As can be seen from FIG. 2, the cable guides 14 each terminate at approximately the same position inside the guide piece 20. At that location, the cable's insulation and shielding usually ends. In other words, when the wires of the cable are to be connected with the contacts 12 of the connector 10, the cable is inserted through the appropriate guide 14, and the insulation and shielding are removed and the end of the cable to expose the individual wires. The cable may then be arranged to allow the individual wires to be accommodated in recesses 22 visible in FIG. 2. Thus, the insulation and shielding of the cable may terminate approximately at the position of the central opening 30, to which the recesses 22 extend.

As can be seen from FIG. 2, in the embodiment shown, the recesses 22 each have a first portion, extending from the opening 30, which extends approximately radially from the opening 30. In other words, the first portions together have a somewhat star-like appearance. Second portions of the recesses 22 extend approximately parallel to each other. In the embodiment shown, the second portions of those recesses which are on different sides of the opening 30, but at approximately the same height along the height direction H, may be aligned with each other. However, the recesses 22 could also be arranged on a single side of the opening 30. When the wires of the cable are to be connected with the contacts 12, individual wires are separated from each other to also accommodate a somewhat star-like or radially extending appearance, and the individual wires are accommodated in the recesses 22. It is noted in this context that the recesses 22 may have one or more flexible parts, portions and/or adaptors, to generally adapt their size to different sizes of wires. For example, one or more recesses 22, may have one or more "half-pipes" having an onion-type structure and suitable to remove as many "layers" as necessary to make the recess large enough for accommodating a particular wire. Such flexible and/or removable parts may be made of rubber. The above-mentioned measures to adapt the recesses 22 to different sizes of wires, is also applicable to other types of recesses, such as recesses 122 shown in FIG. 4 and described in more detail below.

After possibly removing the necessary parts of the recesses 22 and accommodating the wires therein, as described above with reference to FIG. 1, the guide piece 20 is moved towards the contacts 12, so that each wire is pushed into a contact slit (not visible in FIG. 1). To allow this pushing of a wire accommodated in a recess 22 into the slit of contact 12, the guide piece 20 has, on the surface facing the viewer of FIG. 2, a plurality of slots (not shown) for accommodating the contacts 12. The slots may intersect with the recesses 22. In an alternative embodiment, the guide piece 20 may be adapted to fit between contacts aligned along the lateral sides 32 of the guide piece 20 so that wires accommodated in the recesses 22 will also be pushed into the contacts positioned as described above.

Figure 3:
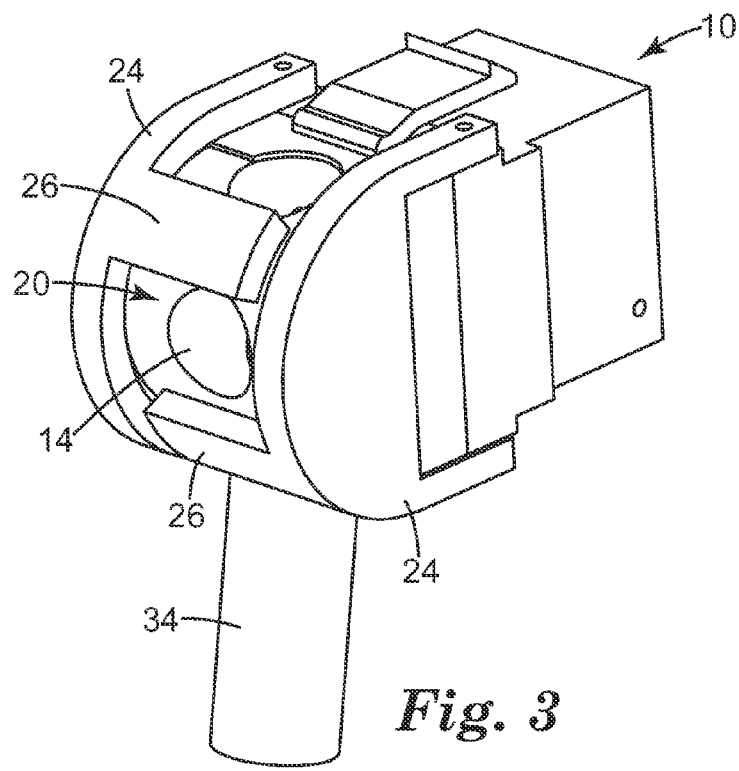
FIG. 3 shows the connector of FIG. 1 with a cable connected therewith.

FIG. 3 shows the connector 10 with a cable 34 connected thereto. In the situation shown in FIG. 3, the cable 34 has been inserted from the bottom side, the guide piece 20 has been moved towards the contacts 12 (see FIG. 1) and the pivotable flaps 24 have been pivoted towards each other to accommodate the guide piece 20 between them. During this movement, the projections 26 have served to push the guide piece 20 in the above-described manner. It can be taken from FIG. 3, that versatility of the connector 10 described herein may be advantageous in that the cable 34 could also be inserted from the top or straight from the rear. In that respect, the wire opening 16, which is exposed at the rear side, is arranged between the two projections 26.

Figure 4:
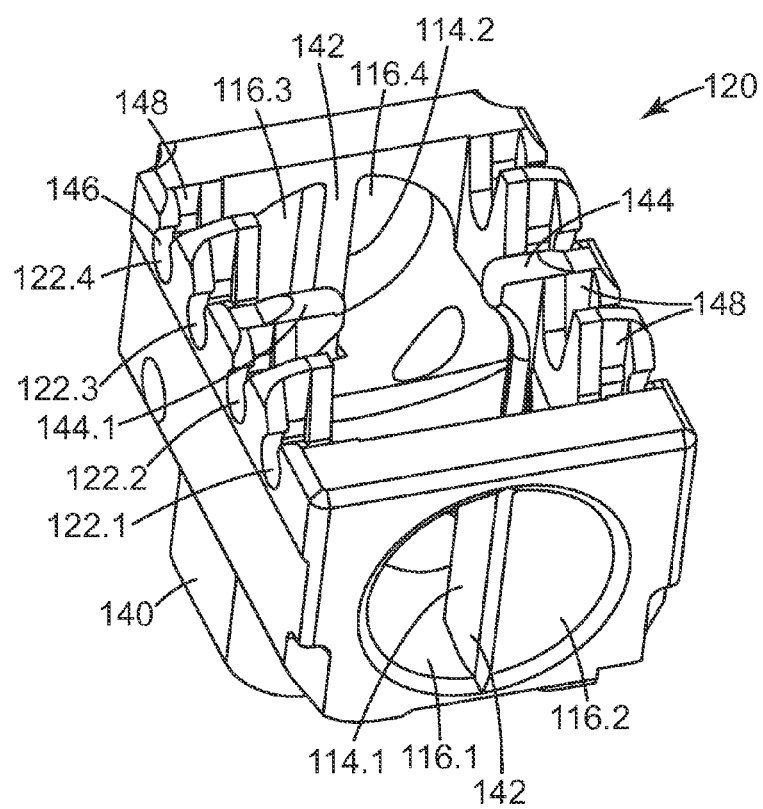
FIG. 4 shows a further embodiment of a guide piece.

FIG. 4 shows a perspective view of another embodiment of a guide piece 120 which may be used in the connector 10 shown in FIGS. 1 and 3 or in another embodiment of a connector. The general appearance of the guide piece 120 differs from that shown in FIG. 2 in that it has the general shape of a cuboid with an extension 140 that generally corresponds to the thickest part of the semi-cylindrical shape of the guide piece 20 shown in FIG. 2. Similar to the guide piece 20 of FIG. 2, openings 116 are exposed in three different directions. Thus, openings 116 visible in FIG. 4 at the front and rear sides are also formed at the lower side (not visible) of FIG. 4.

It may be taken from FIG. 4 that two openings, 116.1 and 116.2 as well as 116.3 and 116.4 are formed in pairs with a web 142 in between. In the embodiment shown, each opening 116 may, for example, be adapted to accommodate four wires, i.e. two pairs of wires. Thus, the insulation and shielding of a cable (not shown) with which eight wires, i.e. four wire pairs, are integrated, may end at the web 142, and the wires may be inserted through the openings 116, for example, four wires through each opening. That part of the web 142 that extends into the interior of the guide piece 120, denoted 114 in the drawing, may serve as a wire guide. In particular, these wire guides 114.1 and 114.2 formed on opposite sides, may be extended into a partition (not shown) and/or may start at a location somewhat "inside" the guide piece 120, i.e. somewhat displaced towards the centre of the guide piece 120. Thus, wires of a left and right side (as oriented in FIG. 4), may be advantageously separated from each other and guided. In such an embodiment, a web (not shown) formed across the openings (not shown) of extension 140 may be coplanar with the webs 142 visible in FIG. 4.

In the embodiment of FIG. 4, four recesses 122 for accommodating wires, described in more detail below, are formed on each side. Moreover, the embodiment shown has, between the second 122.2 and third recess 122.3, i.e., approximately at the center of each side, an internal lug 144 protruding to the interior of the guide piece 120 and serving to separate those wires from each other, which are inserted into the recesses in front of the lug 144, on the one hand, and into the recesses behind the lug 144, on the other hand. In other words, considering four wires, which may, for example, be inserted through the front and left side opening 116.1, two wires of an upper wire pair may, for example, be inserted into recesses 122.1 and 122.2. The wires of a "lower" wire pair may continue at a location below the left side lug 144.1, to recesses 122.3 and 122.4 and may be inserted into these.

As can be seen in FIG. 4, each recess 122 has an entrance 146 which is somewhat narrower than the remainder of the recess 122. The entrances 146 may also be used to clamp wires accommodated therein. This also applies to the remainder of the recesses 122. Moreover, the recess 122 may have an approximately circular cross-section adapted to accommodate wires having, together with their insulation, an approximately circular cross-section as well. When a wire is inserted into a recess 122, the insulation thereof may be briefly compressed, to allow the wire to pass the narrow entrance 146 and the wire then be accommodated in the recess 122. As can be seen from the recesses 122 on the right side of FIG. 4, the recesses may be formed as generally rounded, V-shaped recesses towards the inside of the guide piece 120. In the embodiment shown, there are, between the outer areas of the recesses 122, having the narrow entrance 146, and the inner, generally V-shaped areas of the recesses 120, slots 148 which serve, as mentioned above, to accommodate the contacts 12 (see FIG. 1) and guide the guide piece 120, when the guide piece 120 is pushed towards the contacts.

The present invention has now been described with reference to embodiments thereof. The foregoing detailed description and embodiment have been given for clarity of understanding only. No unnecessary limitations are to be understood there from. For example, all references to sides and directions are exemplary only and do not limit the claimed invention. It will be apparent to those skilled in the art that many changes can be made to the embodiment described without departing from the scope of the invention. Thus, the scope of the present invention should not be limited to the exact details and structures described herein, but rather by the structures described by the language of the claims and the equivalents of those structures.

The invention claimed is:

1. A connector in the field of telecommunications comprising:
   a housing having a rectangular opening on one side unto which a complementary connector can be inserted,
   a plurality of contacts with which wires are connectable inside the connector, and
   a guide piece connected to the connector opposite the side where the complementary connector is inserted, the guide piece having three wire openings disposed on an outside surface of the guide piece and exposed on an outside of the connector distal from the contacts,
   wherein the wire openings are oriented in different directions wherein the housing is provided with at least one pivoted drive piece adapted to drive the guide piece towards the contacts.

2. The connector in accordance with claim 1, wherein at least one guide is formed adjacent at least one wire opening.

3. The connector in accordance with claim 1, wherein the guide piece has at least one recess for accommodating at least one wire, the recess facing the contacts.

4. The connector in accordance with claim 3, wherein the guide piece has at least one slot for accommodating at least one contact.

5. The connector in accordance with claim 4, wherein at least one slot and at least one recess intersect each other.

6. The connector in accordance with claim 1, wherein the drive piece is a pivotable flap having at least one projection adapted to drive the guide piece when the flap is pivoted.

7. The connector in accordance with claim 6, wherein at least two projections are provided, and at least one wire opening is located between two projections.

8. The connector in accordance with claim 1, wherein the connector is a jack or a socket.

9. The connector in accordance with claim 1, wherein the at least three wire openings are oriented in different radial directions from a center region of the connector.

10. The connector in accordance with claim 2, wherein the at least one guide divides the wire opening in pairs or groups of four.

* * * * *

UNITED STATES PATENT AND TRADEMARK OFFICE
CERTIFICATE OF CORRECTION

Page 1 of 1

PATENT NO.       : 7,967,642 B2
APPLICATION NO.  : 12/680948
DATED            : June 28, 2011
INVENTOR(S)      : Schoene et al.

It is certified that error appears in the above-identified patent and that said Letters Patent is hereby corrected as shown below:

Column 10,
Claim 5, Line 32, after "wherein" insert -- the --.
Claim 5, Line 33, after "and" insert -- the --.
Claim 7, Line 39, after "between" insert --the --.

Signed and Sealed this
Twentieth Day of September, 2011

David J. Kappos
*Director of the United States Patent and Trademark Office*